United States Patent
Vaughan et al.

(10) Patent No.: US 11,847,248 B2
(45) Date of Patent: Dec. 19, 2023

(54) AUTOMATED VIEWPOINT DETECTION AND SCREEN OBFUSCATION OF SECURE CONTENT

(71) Applicant: Cigna Intellectual Property, Inc., Wilmington, DE (US)

(72) Inventors: Moses Vaughan, Nutley, NJ (US); Srijit Chandrashekhar Nair, South Windsor, CT (US); Bill Pham, Highlands Ranch, CO (US); Harinath Kasina, Manalapan, NJ (US); Christopher M. Myers, Dublin, OH (US)

(73) Assignee: Cigna Intellectual Property, Inc., Wilmington, DE (US)

( * ) Notice: Subject to any disclaimer, the term of this patent is extended or adjusted under 35 U.S.C. 154(b) by 299 days.

(21) Appl. No.: 17/123,273

(22) Filed: Dec. 16, 2020

(65) Prior Publication Data
US 2022/0188456 A1     Jun. 16, 2022

(51) Int. Cl.
*G06F 21/62* (2013.01)
*G06F 21/35* (2013.01)

(52) U.S. Cl.
CPC .......... *G06F 21/6254* (2013.01); *G06F 21/35* (2013.01); *G06F 2221/032* (2013.01)

(58) Field of Classification Search
None
See application file for complete search history.

(56) References Cited

U.S. PATENT DOCUMENTS

| 8,538,816 | B2 | 9/2013 | Campbell |
| 8,922,480 | B1 * | 12/2014 | Freed .................. G06F 21/6245 382/103 |
| 8,957,847 | B1 | 2/2015 | Karakotsios |

(Continued)

FOREIGN PATENT DOCUMENTS

| EP | 3057053 A1 | 8/2016 |
| EP | 3483763 A1 | 5/2019 |
| EP | 3642692 A1 | 4/2020 |

OTHER PUBLICATIONS

Advanced Eye Tracking and Biometric Platform; https://tech.tobii.com/technology/is5-platform, accessed as early as May 20, 2020.

(Continued)

*Primary Examiner* — Michael Pyzocha
(74) *Attorney, Agent, or Firm* — Harness IP

(57) ABSTRACT

A smart mirror system includes a screen configured to generate a display for viewing by a user, a mirror positioned in front of the screen, a near-field-communication (NFC) card reader located behind the mirror, a network interface for communicating with a remote health data server, memory configured to store computer-executable instructions, and at least one processor configured to execute the instructions. The instructions include selectively detecting, by the NFC card reader, an NFC chip of a member card placed in proximity to the NFC card reader. The instructions include, in response to detecting the NFC chip, obtaining member information from the detected NFC chip, and authenticating the user to the remote health data server, via the network interface, according, at least in part, to the obtained member information.

11 Claims, 12 Drawing Sheets

(56) References Cited

U.S. PATENT DOCUMENTS

| | | | |
|---|---|---|---|
| 9,355,612 B1* | 5/2016 | Shepard | G06F 3/0304 |
| 9,536,097 B2 | 1/2017 | Anderson | |
| 9,703,990 B2 | 7/2017 | Cohen | |
| 9,965,860 B2 | 5/2018 | Nguyen | |
| 10,025,938 B2 | 7/2018 | Krishnamurthi | |
| 10,185,843 B2 | 1/2019 | Moore | |
| 10,503,925 B1 | 12/2019 | Hadsall | |
| 10,503,935 B1* | 12/2019 | Hadsall | G06F 21/32 |
| 10,607,035 B2 | 3/2020 | Jones | |
| 10,635,167 B2 | 4/2020 | Kempinski | |
| 11,227,060 B1* | 1/2022 | John | G06F 21/606 |
| 11,449,634 B2* | 9/2022 | Larson | H04L 63/0421 |
| 2006/0262140 A1 | 11/2006 | Kujawa | |
| 2010/0205667 A1* | 8/2010 | Anderson | G06F 3/017 726/19 |
| 2013/0205410 A1 | 8/2013 | Sambamurthy | |
| 2014/0145966 A1 | 5/2014 | Gardenfors | |
| 2014/0259184 A1 | 9/2014 | Hoyer | |
| 2015/0234457 A1 | 8/2015 | Kempinski | |
| 2016/0063549 A1 | 3/2016 | Fuchs | |
| 2016/0070344 A1* | 3/2016 | Gohl | G09G 5/377 345/156 |
| 2016/0132721 A1* | 5/2016 | Bostick | G06F 3/013 382/118 |
| 2016/1565751 | 6/2016 | Jin-Hong | |
| 2016/0210473 A1* | 7/2016 | Cohen | G06F 21/6245 |
| 2017/0040002 A1* | 2/2017 | Basson | G06F 3/147 |
| 2017/0097679 A1 | 4/2017 | Kempinski | |
| 2017/0255786 A1* | 9/2017 | Krishnamurthi | G06F 21/32 |
| 2018/0082068 A1* | 3/2018 | Lancioni | G06F 21/84 |
| 2018/0239931 A1* | 8/2018 | Ziaja | G06F 21/62 |
| 2018/0285592 A1* | 10/2018 | Sharifi | G06F 21/84 |
| 2019/0087082 A1* | 3/2019 | Chaudhri | G06F 3/0481 |
| 2019/0138740 A1* | 5/2019 | Ricknäs | G06F 3/04842 |
| 2020/0034575 A1* | 1/2020 | Wu | G06F 21/74 |
| 2020/0081529 A1 | 3/2020 | Richmond | |
| 2020/0104539 A1* | 4/2020 | Liu | G06F 21/629 |
| 2020/0226966 A1* | 7/2020 | Shin | G09G 3/2003 |
| 2020/0349296 A1* | 11/2020 | Young | G09C 5/00 |
| 2021/0042520 A1* | 2/2021 | Molin | G06V 40/18 |
| 2021/0150076 A1* | 5/2021 | Hinkle | G06F 21/31 |
| 2021/0182439 A1* | 6/2021 | Singh | G06F 21/629 |
| 2021/0390215 A1* | 12/2021 | Sangle-Ferriere | G06F 21/84 |

OTHER PUBLICATIONS

Brand et al., Enabling Strong Authentication with WebAuthn; https://developers.google.com/web/updates/2018/05/webauthn, accessed as early as May 20, 2020.

Democratizing Webcam Eye Tracking on the Browser, https://webgazer.cs.brown.edu/, accessed as early May 20, 2020.

Designing for Humans, https://www.designingforhumans.com/idsa/2012/09/human-factors-guidelines-what-the-fda-can-learn-from-the-nhs.html, Sep. 18, 2012.

Evans, What is Pupillary Distance and How Do You Measure It; https://www.allaboutvision.com/eye-care/measure-pupillary-distance/, Aug. 2019.

Genco, What Eye-Tracking Can and Can't Tell You About Attention, https://www.nmsba.com/buying-neuromarketing/neuromarketing-techniques/what-eye-tracking-can-and-cant-tell-you-about-attention, Neuromarketing Science & Business Association, accessed as early as May 20, 2020.

Github, https://github.com/brownhci/WebGazer, accessed as early as May 20, 2020.

How to Calculate a Display's Pixel Density (ppi/Pixels Per Inch); https://turbofuture.com/computers/How-To-Calculate-Pixel-Density-ppi-By-Yourself-And-What-Is-Pixel-Density, accessed as early as May 20, 2020.

https://github.com/opengazer/OpenGazer, accessed as early as May 20, 2020.

Imarc, What's the best font size for the web? Well, it depends . . . https://www.imarc.com/blog/best-font-size-for-any-device, Jan. 8, 2016.

Korpela, http://jkorpela.fi/x-height.html, May 12, 2017.

Krišto, Mate, and Marina Ivasic-Kos. "An overview of thermal face recognition methods." 2018 41st International Convention on Information and Communication Technology, Electronics and Microelectronics (MIPRO). IEEE, 2018.

Legge, et al. http://jov.arvojournals.org/article.aspx?articleid=2191906, Journal of Vision, Aug. 2011.

Legge, et al., The case for the visual span as a sensory bottleneck in reading, http://jov.arvojournals.org/article.aspx?articleid=2122415, Journal of Vision, Mar. 2007.

Li, Zhuqi, et al. "Look into my eyes: Fine-grained detection of face-screen distance on smartphones." 2016 12th International Conference on Mobile Ad-Hoc and Sensor Networks (MSN). IEEE, 2016.

Oasis, http://docs.oasis-open.org/office/v1.2/os/OpenDocument-v1.2-os-part1.html#_RefHeading_1419432_253892949, Sep. 29, 2011.

Rayner, Keith. "Eye movements in reading and information processing: 20 years of research." Psychological bulletin 124.3 (1998): 372.

Trusted Computing Group, https://trustedcomputinggroup.org/resource/trusted-platform-module-tpm-summary; accessed as early as May 20, 2020.

Using Data Attributes, https://developer.mozilla.org/en-US/docs/Learn/HTML/Howto/Use_data_attributes, accessed as early as May 20, 2020.

Windows Hello for Business and Authentication, https://docs.microsoft.com/en-us/windows/security/identity-protection/hello-for-business/hello-how-it-works-authentication; accessed as early as May 20, 2020.

Windows Scaling Issues for High-DPI devices; https://support.microsoft.com/en-us/help/3025083/windows-scaling-issues-for-high-dpi-devices, accessed as early as May 20, 2020.

Woodford, https://www.explainthatstuff.com/how-iris-scans-work.html; accessed as early as May 20, 2020.

* cited by examiner

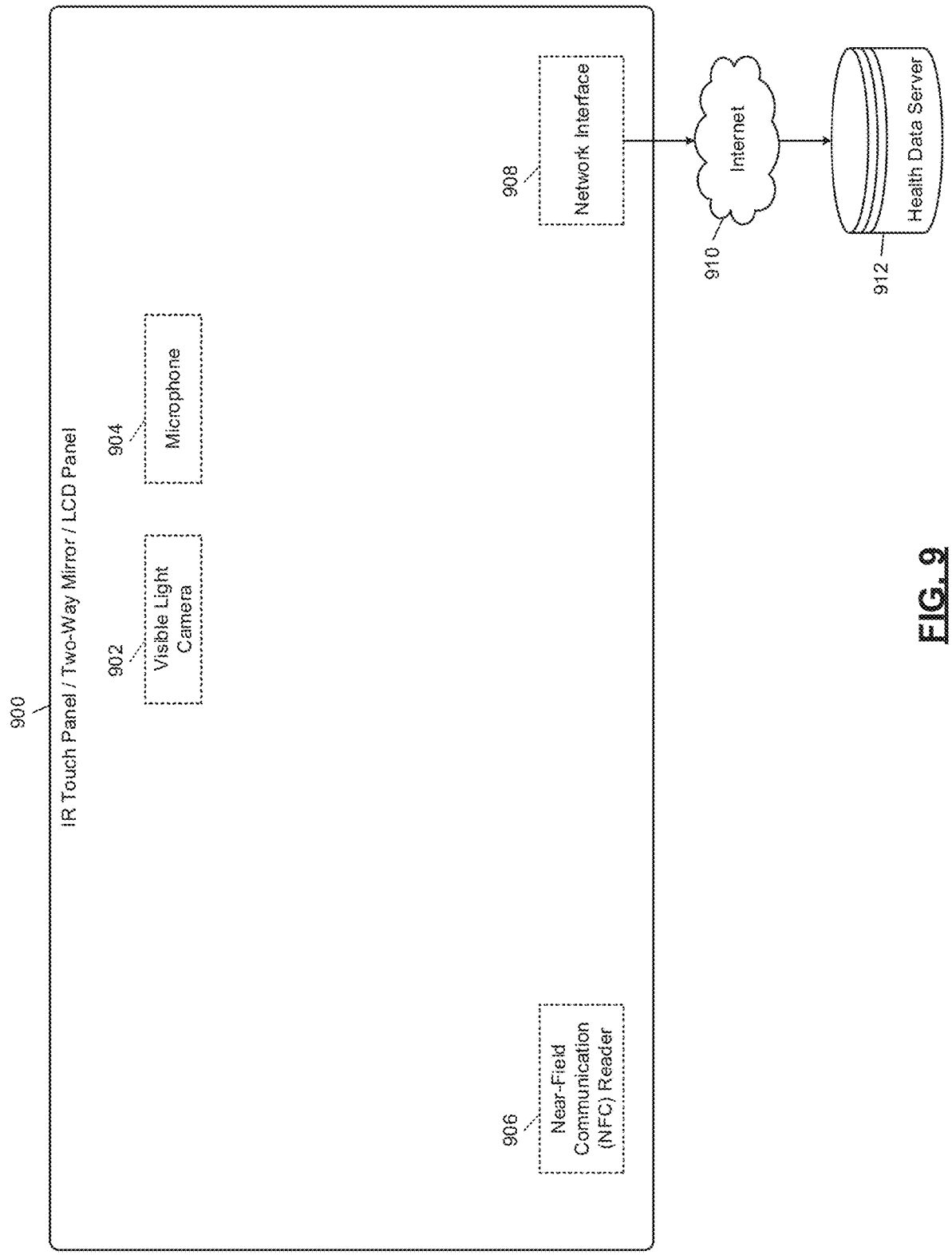

AUTOMATED VIEWPOINT DETECTION AND SCREEN OBFUSCATION OF SECURE CONTENT

FIELD

The present disclosure relates to automated viewpoint detection and screen obfuscation of secure content.

BACKGROUND

Sensitive data such as patient health data, credit card and financial account information, etc., is often displayed on screens that may be viewable by unintended third parties that are not authorized to view the sensitive or secure data. For example, some open office environments include workstations where many people may be located in close proximity and able to view each other's screens, employees may work in public environments such as libraries or coffee shops, employees may work from home where family members or friends are able to view a user's screen periodically, etc. In each of these situations, highly sensitive data may be displayed while the setting is not secured. For example, highly sensitive PHI/PII data should be protected from those who are not authorized to view the data, even while an authorized user is working on the data. Even with strong end-to-end encryption, passwords, or firewalls, unauthorized viewers of the screen may jeopardize the integrity of secure data.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A system includes a screen configured to display documents for viewing by at least one authorized user, memory configured to store computer-executable instructions, an authorized user database, and a document properties database, and at least one processor configured to execute the instructions. The instructions include identifying one or more secure content portions of a document to be displayed on the screen, according to the document properties database, detecting a viewer at a viewing proximity location with respect to the screen, determining whether the detected viewer is authorized to view the secure content portions according to the authorized user database. In response to a determination that the detected viewer is not authorized to view the secure content portions, the method includes determining a gaze location of the unauthorized viewer on the screen. In response to the gaze location encompassing the identified one or more secure content portions of the document, the instructions include obfuscating the identified one or more secure content portions of the document.

In other features, the instructions further include obtaining a translation of the identified one or more secure content portions of the document, and storing the translation in the document properties database, and the obfuscating includes displaying the translation of the identified one or more secure content portions of the document. In other features, the obfuscating includes rendering the identified one or more secure content portions of the document illegible, the document includes one or more non-secure content portions, and the obfuscating includes leaving the one or more non-secure content portions legible.

In other features, the instructions further include displaying the identified one or more secure content portions with obfuscation by default until an authorized viewer is detected at the viewing proximity location with respect to the screen, or displaying the identified one or more secure content portions without obfuscation by default until an unauthorized viewer is detected at the viewing proximity location with respect to the screen with a determined gaze location encompassing the identified one or more secure content portions of the document.

In other features, the obfuscating includes removing at least one of the identified one or more secure content portions from the screen, and the instructions further include displaying the removed at least one secure content portion from the screen in response to a detection that the unauthorized viewer has left the viewing proximity location with respect to the screen. In other features, determining whether the detected viewer is authorized includes at least one of capturing an infrared thermogram of the detected viewer and comparing the captured infrared thermogram to entries in the authorized user database, capturing a visible light image of the detected viewer and comparing the captured visible light image to entries in the authorized user database, capturing a biometric marker of the detected viewer and comparing the captured biometric marker to entries in the authorized user database, displaying multiple images or multiple numbers in a random pattern on the screen, receiving an input selection sequence of the multiple images of the multiple numbers from the detected viewer, and comparing the input selection sequence to entries in the authorized user database, and capturing a motion gesture of the detected viewer and comparing the captured motion gesture to entries in the authorized user database.

In other features, the determining the gaze location of the detected viewer includes emitting an infrared light beam, capturing a reflection of the infrared light beam using one or more cameras, and filtering and triangulating the captured reflection to identify the gaze location of the detected viewer. In other features, the instructions further include, in response to the gaze location encompassing the identified one or more secure content portions of the document, determining whether a viewing angle of the detected viewer is greater than a deciphering angle threshold, and only obfuscating the identified one or more secure content portions of the document in response to a determination that the viewing angle of the detected viewer is greater than the deciphering angle threshold.

In other features, determining whether the viewing angle of the detected viewer is greater than the deciphering angle threshold includes calculating an x-height percentage of a font of text in the document, calculating a visual angle and perceived x-height of the text in the document, determining a distance of the detected viewer from the screen, and comparing the perceived x-height and the determined distance to the deciphering angle threshold. In other features, determining the distance of the detected viewer from the screen includes at least one of using a laser of a LIDAR system, at least in part, to determine the distance of the detected viewer from the screen, capturing an image of the detected viewer, measuring an inter-pupillary distance of the detected viewer, and calculating the distance of the detected viewer from the screen according, at least in part, to the measured inter-pupillary distance.

In other features, the instructions further include, in response to the gaze location encompassing the identified one or more secure content portions of the document determining whether a viewing time of the detected viewer is greater than a deciphering time threshold, and only obfuscating the identified one or more secure content portions of the document in response to a determination that the viewing time of the detected viewer is greater than the deciphering time threshold. In other features, determining whether the viewing time of the detected viewer is greater than the deciphering time threshold includes monitoring eye movements of the detected viewer by capturing reflections of emitted infrared light beams off of eyes of the detected viewer, measuring a fixation period duration during which the eyes of the detected viewer are stationary, and comparing the measured fixation period duration to the deciphering time threshold.

In other features, the detecting includes detecting at least two viewers at the viewing proximity location with respect to the screen, the determining whether the detected viewer is authorized includes determining whether a set of the at least two detected viewers is authorized, by comparing a combination of detected features of the at least two detected viewers to a plurality of multi-user set entries in the authorized user database, and the instructions further include displaying the identified one or more secure content portions with obfuscation by default until all members of one of the multi-user set entries are detected at the viewing proximity location with respect to the screen, and obfuscating the identified one or more secure content portions in response to detection of an unauthorized viewer in addition to all members of the one of multi-user set entries.

A smart mirror system includes a screen configured to generate a display for viewing by a user, a mirror positioned in front of the screen, a near-field-communication (NFC) card reader located behind the mirror, a network interface for communicating with a remote health data server, memory configured to store computer-executable instructions, and at least one processor configured to execute the instructions. The instructions include detecting, by the NFC card reader, an NFC chip of a member card placed in proximity to the NFC card reader, in response to detecting the NFC chip, obtaining member information from the detected NFC chip, and authenticating the user to the remote health data server, via the network interface, according, at least in part, to the obtained member information.

In other features, the authenticating includes storing a token in the memory to establish the authentication of the user to the remote health data server. In other features, the instructions further include presenting the token to the remote health data server in response to identifying the user via at least one of facial recognition and voiceprint recognition.

In other features, the instructions further include displaying a location of the NFC card reader on the screen in response to a determination that the user is attempting to log in to the smart mirror. In other features, the instructions further include determining whether the user is authorized to view text of the generated display, and in response to a determination that the user is not authorized to view the text of the generated display, obfuscating the text of the generated display.

In other features, determining whether the user is authorized includes at least one of displaying multiple images or multiple numbers in a random pattern on the screen, and receiving an input selection sequence of the multiple images of the multiple numbers from the user, and capturing a motion gesture of the user. In other features, the smart mirror system includes a touch panel proximate to the mirror to receive inputs from the user, the screen comprises a liquid crystal display panel, the touch panel comprises an infrared touch panel, and the smart mirror system includes at least one of a camera for capturing a facial image of the user and a microphone for capturing a voiceprint of the user.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

FIG. 9 is a block diagram of an example smart mirror system.

In the drawings, reference numbers may be reused to identify similar and/or identical elements.

DETAILED DESCRIPTION

Figure 1:
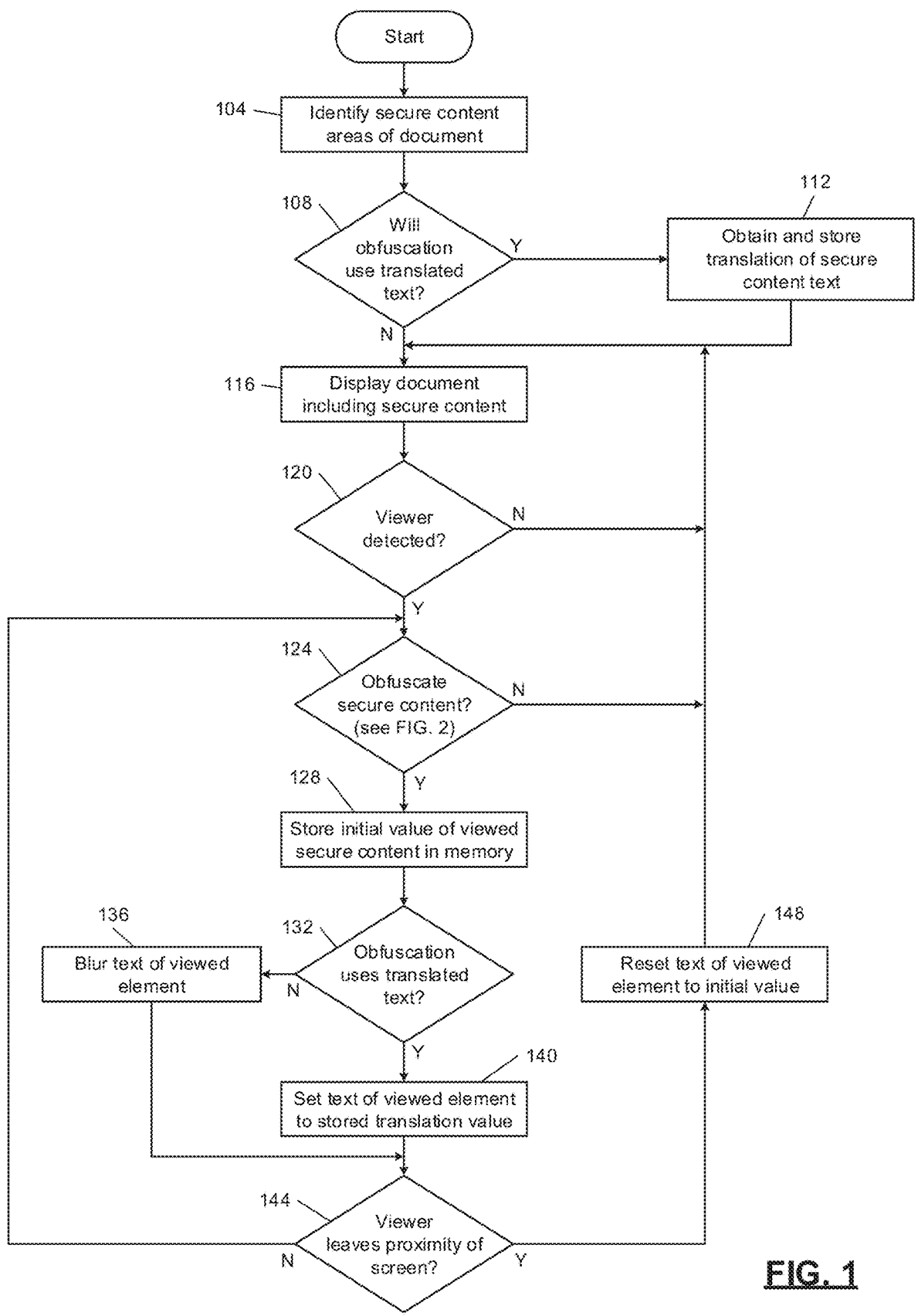
FIG. 1 is a flowchart depicting an example method of automated viewpoint detection and screen obfuscation of secure content.

In various implementations, sensitive contents on a shared or otherwise viewable screen may be obfuscated when sensitive content is being displayed and viewed by an unauthorized viewer. Approaches for obfuscating content may be implemented in any suitable environment, such as an office, a healthcare setting including monitors and tablets with charting information, pharmacies that display prescription information on check out terminals, ATM machines, point-of-sale devices, mobile devices, etc. For example, a multi-tenant system may allow for registration of multiple authorized users, such as via a facial scanning onboarding process, and detected viewers of the screen that are not authorized may be considered as potential threats to the integrity of sensitive data in the screen contents. Screen contents may be classified as secure or insecure, and example screen contents include portions of an application, lines of a text document, images or videos, generic portions of the screen, etc. The various screen contents may be labeled as belonging to a security context, meaning that only validated users are able to view the secured content portions.

All viewers of the screen may be recognized in near real-time, and classified as valid or non-valid viewers. If non-validated users are attempting to view secure content on the screen, the secure content may be obfuscated. For example, text may be obfuscated by subtly changing the character set such as changing readable characters to other random characters, or even another language, or yet more obvious obfuscation may be employed such as rendering the secure contents illegible via blurring, redaction, removing secure contents from the display, etc. When the unauthorized user stops viewing the screen or a secure portion of the screen, the text may be unobscured so that the text is plainly visible again to an authorized user.

Authorized users may be enrolled into a validation set (such as by storing user credentials in an authorized user database that stores information about which users are authorized to view what content), which provides access roles for the system. The validation set may be exclusive to a specific device, to a range of devices, etc. Example enrollment processes may include facial recognition, iris scanning systems, etc., and may include digital photographs of the user's face and eyes, using ordinary light, using invisible infrared right, etc. Using infrared camera technology may enable a device to consistently identify people in wide-ranging lighting conditions, as well as allowing for subtle changes in appearance including facial hair, cosmetic makeup, etc. Regarding iris recognition, infrared may display unique features such as darkly colored eyes that would not stand out clearly in ordinary light. The two digital photographs (e.g., ordinary image and infrared image) may be further analyzed to remove unnecessary details such as eyelashes, etc., and then used to identify a large number of features that are unique to each face. The features may be stored in a secure chip for privacy purposes, such that the user's biometric face and digital fingerprint will not leave the device, and an asymmetric cryptography key can be used to obtain an access token for the user.

In various implementations, multiple conditions may have to be satisfied before obfuscating displayed text. For example, before obfuscating text, a system may have to determine that the user is not authorized to view the secure content on the screen, that the user's location allows the user to decipher what is viewable on the screen, may determine the distance of the user from the screen, may determine which portion of the screen the user is looking at, may determine whether the portion that is currently viewed contains secure content, etc. In various implementations, more or less (or other) conditions may be checked by the system prior to obfuscating text.

Automated Screen Obfuscation

FIG. 1 illustrates an example process for automated viewpoint detection and screen obfuscation of secure content. At 104, control begins by identifying secure content areas of a document. For example, a document displayed on the screen may include various text portions, graphical images or videos, etc., and control may identify which portions of the document contain secure content that should be protected from unauthorized viewing (for example, by consulting a document properties database the stores details about documents such as locations of secure content within the documents). Secure content may include PHI/PII data, sensitive financial information, etc.

At 108, control determines whether the obfuscation will use translated text. For example, in various implementations, when text is obfuscated the text may be converted to translated text so that the unauthorized viewer does not immediately recognize the text as being obfuscated. This may allow for an authorized viewer that understands multiple languages to continue reading the translated text, while the unauthorized viewer cannot understand the translated text. If it is determined that the application will use translated text at 108, control proceeds to 112 to obtain and store a translation of the secure content text. For example, any portions of the document that are identified as secure may be supplied to a system for machine translation, where the machine translation is stored for use during future obfuscation, etc.

After obtaining and storing the translation of the secure content text at 112, or after determining that the application will not use translated text for obfuscation, control proceeds to 116 to display the document including the secure content. As shown in the example of FIG. 1, the document text may be displayed until a viewer is detected. In other implementations, control may wait until a user has been authorized before any data is displayed, or before secure content is displayed. At 120, control determines whether a viewer is detected. If not, control loops back to 116 to continue displaying the document and waiting for detection of a viewer.

If a viewer is detected at 120, control proceeds to 124 to determine whether to obfuscate content of the document. Further details of how control may determine whether the content should be obfuscated are provided in FIG. 2, and described further below. Returning to FIG. 1, if control determines not to obfuscate the secure content at 124, control loops back to 116 to continue displaying the document including the secure content.

If control determines to obfuscate secure content at 124, control proceeds to 128 to store an initial value of the secure content as displayed in its non-obfuscated format, for later display once the unauthorized viewer leaves the screen. At 132, control determines whether the obfuscation will use translated text. This determination may be similar to the determination 108. If control determines that the obfuscation will not use translated text at 132, control proceeds to 136 to blur the text of the viewed element. For example, the secure text that the unauthorized viewer is looking at may be blurred (or alternatively redacted, changed to symbols, etc.), so the unauthorized user cannot read the secure text. Alternatively, if control determines at 132 that the obfuscation will not use translated text, control may proceed to 140 to set the text of the secure content to the stored translation value. For example, control may replace any secure content that the unauthorized viewer is looking at with translated text that the unauthorized user will not be able to understand. This text may be obtained from the previously stored translated text for quick obfuscation that does not require real-time translation.

At 144, control determines whether the viewer has left the proximity of the screen. If not, control loops back to 124 to determine whether to continue obfuscating the secure content. Once control determines at 144 that the viewer has left the proximity of the screen, control proceeds to 148 to reset the text of the viewed element to its initial value. For example, control may remove the obfuscation to display the secure text normally as it was prior to the unauthorized viewer looking at the screen. Control then returns to 116 to display the document including the secure content.

Figure 2:
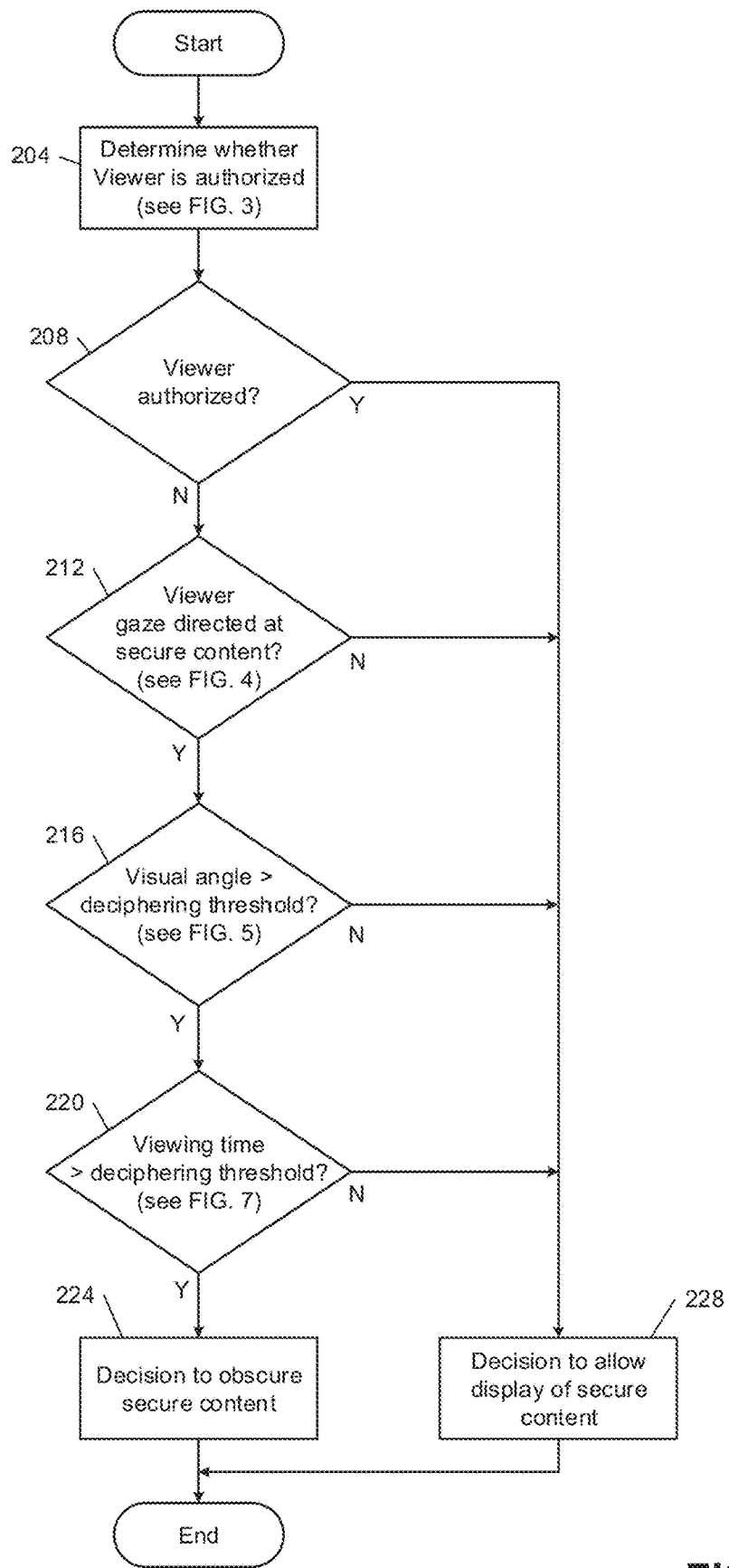
FIG. 2 is a flowchart depicting an example method for determining whether secure content of a screen should be obfuscated.
Figure 3:
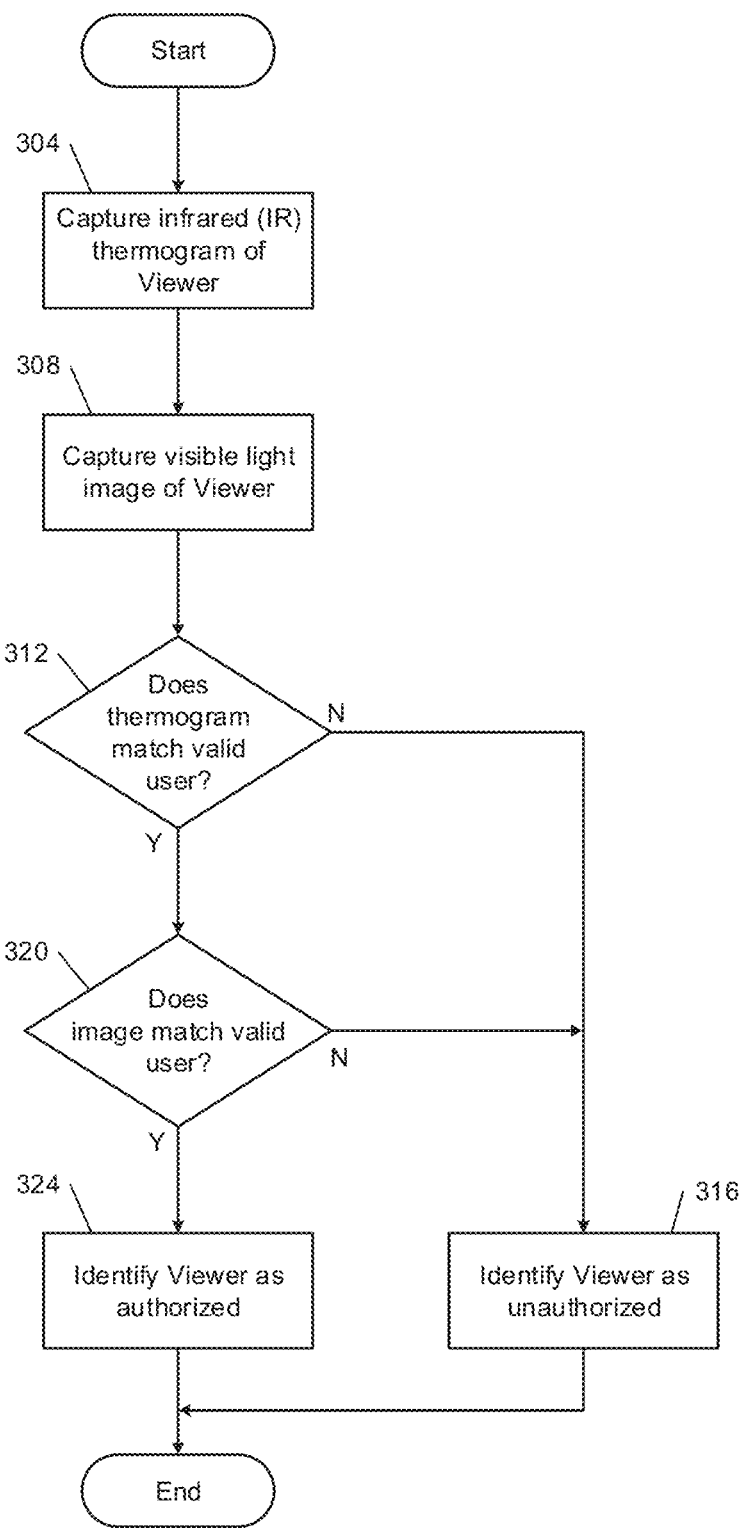
FIG. 3 is a flowchart depicting an example method for determining whether the viewer is authorized to view secure content.

FIG. 2 illustrates an example process for determining whether secure content of a screen should be obfuscated. At 204, control starts by determining whether the viewer is authorized to view secure content. FIG. 3 provides further details on how control may determine whether a viewer is authorized, which are described further below. Referring again to FIG. 2, at 208 control checks whether the viewer has been determined as authorized or not. If the viewer is authorized, control proceeds to 228 to issue a decision to allow displaying of secure content.

If control determines at 208 that the viewer has not been authorized to view secure content of the screen, control proceeds to 212 to determine whether the viewer's gaze is directed at secure content. Additional details for how to determine the direction of the viewer's gaze are described further below with reference to FIG. 4. Returning to FIG. 2, if control determines at 212 that the viewer's gaze is not directed at secure content, control proceeds to 228 to issue the decision to allow displaying of the secure content. For example, even if control determines that the viewer of the screen is not authorized to view secure content, if the viewer is not actually directing their gaze at the secure content (e.g., the user is looking at other non-secure portions the screen), control may still allow the secure content to be displayed at least until the viewer changes their gaze location to the secure content.

If control determines at 212 that the viewer is directing their gaze at the secure content, control proceeds to 216 to determine whether the visual angle of the viewer is greater than a text deciphering threshold. Additional details for determining the visual angle with respect to the text deciphering threshold are provided below with reference to FIG. 5. Referring again to FIG. 2, if control determines at 216 that the user's visual angle is not greater than the deciphering threshold (e.g. the viewer is not likely to be able to actually decipher the secure text based on the angle that the viewer is using to look at the screen), control proceeds to 228 to allow displaying of the secure content. For example, even if a user is directing their gaze at secure portions of the screen, the visual angle of the user may not allow the user to actually decipher the text of the screen (because the user is too far away, etc.). In that case, control may continue to allow the text to be displayed without obfuscation, at least until the user improves their visual angle to be able to decipher the text.

If control determines at 216 that the viewer's visual angle is greater than the text deciphering threshold, control proceeds to 220 to determine whether the viewer's viewing time is greater than a viewing time deciphering threshold. Additional details regarding the determination of whether the viewer's viewing time is greater than the deciphering threshold are provided further below with reference to FIG. 7. Returning again to FIG. 2, if control determines at 220 that the viewer's viewing time is not greater than deciphering threshold, control proceeds to 228 to issue the decision to allow displaying of the secure content. For example, even if the viewer is directing their gaze at a secure portion of the screen with a sufficient visual angle, the viewer may not be looking at the screen long enough to actually understand and decipher the text. In that case, control may be continued to allow display of the secure text without obfuscation, at least until the viewer's gaze exceeds the deciphering threshold time.

If control determines at 220 that the viewer's viewing time is greater than the deciphering threshold time period, control proceeds to 224 to issue a decision to obscure the secure content. For example, if control determines that the viewer is directing their gaze at secure content with a sufficient visual angle and viewing time to understand the content, and the user is not authorized, control may determine to obfuscate the secure content to prevent the unauthorized viewer from obtaining the secure information. Although FIG. 2 illustrates four different conditions to be met in order to obfuscate the secure content, various implementations may include more or less (or other) conditions that need to be met prior to obfuscating the secure content. For example, various implementations may not require a viewing time determination, may not require a visual angle termination, may not require a gaze direction determination, etc. In various implementations, the example conditions shown in FIG. 2 may be combined with other conditions in order to determine whether or not to obfuscate secure content.

FIG. 3 illustrates an example process for determining whether the viewer is authorized to view secure content. At 304, control captures an infrared (IR) thermogram of the viewer. At 308, control captures a visible light image of the viewer. Although FIG. 3 illustrates first capturing a thermogram, and then capturing a visible light image, in various implementations only one or the other of the images may be captured, images may be captured at the same time in parallel, other types of images may be captured, etc.

At 308, control determines whether the thermogram image matches a stored entry for a valid user. For example, a thermal infrared camera may capture heat emitted from a subject and form an image using IR radiation, often referred to as a thermographic. These IR images have the capability to capture both anatomical and physiological face information, such as a structure of the blood vessels and facial vascular network of the user. These features may be compared using a classification that looks for matches based on the unique biometric features of each person within the validation set. If control determines that the thermographic does not match any valid users that 312, control proceeds to 316 to identify the viewer as unauthorized.

If control determines at 312 that the thermogram does match a valid user, control proceeds to 320 to determine whether the visible light image matches a valid user. For example, a comparison of the visible light image to stored valid user images may be used to provide redundant verification for authorized users. If control determines at 320 that the visible image does not match any valid user, control proceeds to 316 to identify the user as unauthorized. If control determines at 320 that the visible light image does match a valid user, control proceeds to 324 to identify the viewer as authorized. Although FIG. 3 illustrates the thermographic and visible light image determinations as is taking place one after another, in various implementations the determinations may be made in parallel, only one or the other of the determinations may be used to identify the viewer as authorized or unauthorized, other authentication procedures may be used in addition to the thermographic and/or visible light images, etc.

In various implementations, a multiuser system may have the capability to classify multiple valid users. Each user may be provided with a unique authentication and access token, which may allow for authenticating multiple security tokens to a single endpoint. In contrast to existing security mechanisms that only account for a single user entering either a username and password combination or a biometric input, various implementations described herein may provide a multi-user authentication approach. If a user is utilizing multiple devices simultaneously, the user may be logged out of other unused devices for added security, by having any accesses to those other devices rejected. Allowing multiple users to log in to a single device may allow multiple people to view secure data at once, such as a team of authorized employees working on the same PHI data while an intern or unauthorized employee outside of the team is restricted to viewing only non-obfuscated text that is not sensitive. In additional examples, joint members of a shared bank account may be allowed to view the same bank account information while external onlookers are obfuscated, application developers may be allowed to view confidential code while unauthorized users are obfuscated, etc. In these cases, two or more authorized users may be allowed to view the same secure content, while the text is obfuscated if additional unauthorized users attempt to view the secure content.

Figure 4:
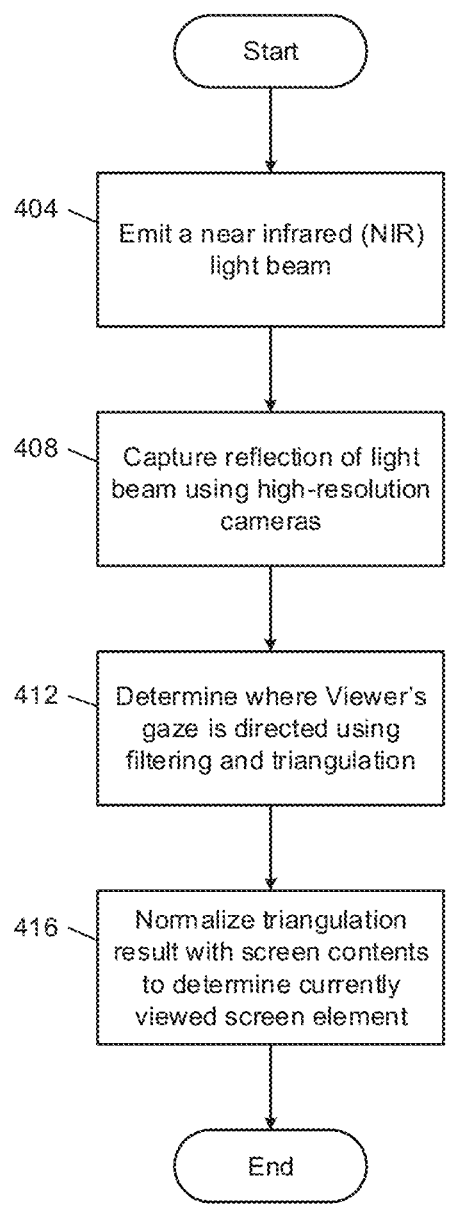
FIG. 4 is a flowchart depicting an example method for determining whether a viewer's gaze is directed at secure content.

FIG. 4 illustrates an example process for determining whether a viewer's gaze is directed at secure content. In various implementations, suitable eye tracking approaches may be used to determine where a person is looking within the perimeter of a screen. For example, software approaches, hardware approaches, etc., may be used to identify a viewer's gaze location on the screen, such as a technique known as pupil center corneal reflection (PCCR). At 404, control emits a near infrared light beam, which is reflected in the viewer's eyes. The infrared light is part of the non-visible spectrum of light, and therefore the viewer will not see or detect the infrared light.

At 408, control captures a reflection of light beam using high-resolution camera(s), and then control proceeds to 412 to determine where the viewer's gaze is directed using filtering and triangulation. For example, an eye tracker may determine where the user is looking based on gaze point movement calculations. Triangulation is normalized at 416, with reference to what is displayed currently on the screen, in order to determine which element of the screen is being viewed currently.

In various implementations, an embeddable modular platform for eye tracking may be integrated into a product, such as a convenient system-on-a-chip solution. Other less precise software only solutions may be used, such as free open-source formats. Although FIG. 4 illustrates one example process for determining the location of a viewer's gaze on the screen, various implementations you use any other suitable approaches for determining where the user is looking on the screen.

Figure 5:
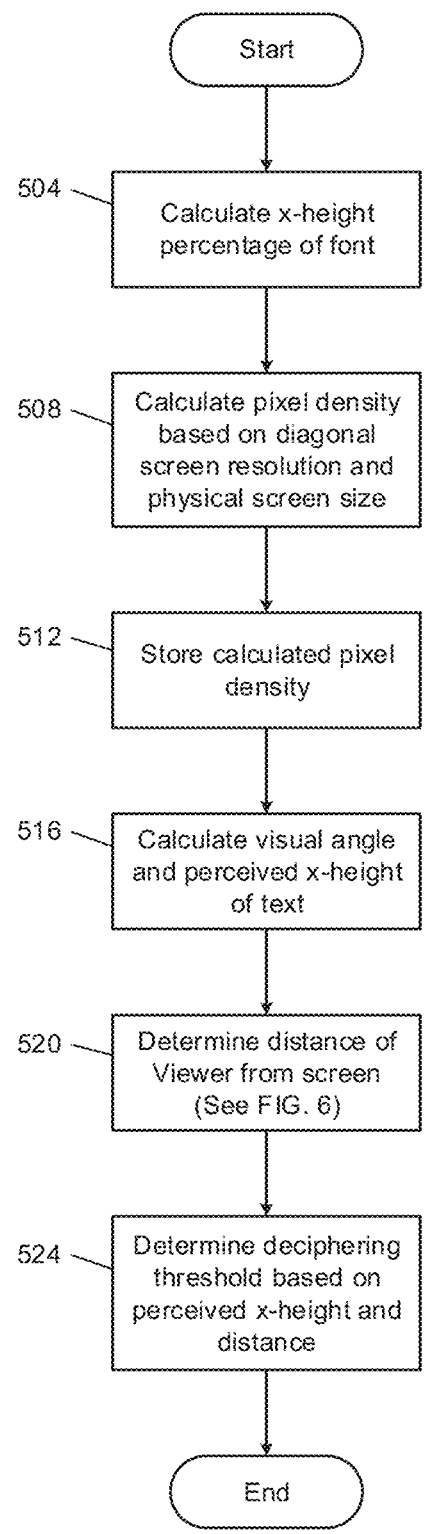
FIG. 5 is a flowchart depicting an example method for determining whether a viewer's visual angle is greater than a deciphering threshold.

FIG. 5 illustrates an example process for determining whether a viewer's visual angle is greater than a deciphering threshold. Whether a viewer can decipher content on a screen may depend on a number of variables, such as distance, illumination, contrasting colors, viewing angle, visual acuity of the viewer, etc. Due to the sensitive nature of secure content, in various implementations the system may assume optimal environmental factors (e.g., optimal illumination, contrasting colors, viewing angle, etc.), as well as optimal visual acuity of the viewer. A primary factor for decipherability in many cases is the angular size of an object as it relates to the viewer's eye. An object which is closer will inherently take up a larger visual angle as compared to an object that is farther away and will take up a smaller visual angle. The size at which clear visibility is compromised may be considered as a limit on decipherability. In various implementations, decipherability may depend on various factors including a text font, a pixel density, etc.

Angular size of text inherently increases as the viewer moves closer, thereby making it easier to read. Ocular angles are typically measured in radians or degrees, while font size is measured in points. Points is a physical unit of measure where there are normally 72 points per inch. All fonts begin at a set baseline, and within a font there are constant heights dedicated for the upper bound border of capital letters as well as the upper bound border of lower-case letters (known as the x-height). The x-height can change across various fonts, and is used as a relative measure within a given point value. For example the font Arial has an x-height of 0.519, Calibri has an x-height of 0.466, Cambria has an x-height of 0.466, Tahoma has an x-height of 0.545, and Verdana has an x-height of 0.545. As shown in FIG. 5, at 504, control begins by calculating an x-height percentage of the font of the displayed secure text.

At 508, control calculates a physical pixel density (PPI) based on a diagonal resolution of the screen, and the physical screen size. The diagonal resolution is acquired via the Pythagorean Theorem, where the width and height resolutions of a screen are divided by the diagonal screen sizing. An example formula for the PPI is as follows:

$$\text{pixel density} = \frac{\sqrt{\text{width}^2 + \text{lenght}^2}}{\text{screen size (diagonal)}} \quad \text{Equation 1}$$

According to Equation 1, for a 4K (3840×2160) resolution screen having a size of 24 inches, the diagonal resolution would be 4406. Logical pixel density, on the other hand, is a virtual representation of density that an operating system's window manager provides an application to render onto. Applications render themselves onto a standard sized virtual representation, which is then scaled to variable sized physical screens. Microsoft Windows assumes a 96 PPI, so the logical pixel density may be accounted for when measuring text size on various screens. At 512, control stores the calculated pixel density.

At 516, control calculates a visual angle and perceived x-height of the secure content text. For example, visual acuity may be measured in terms of the size of an angle for which an object (e.g., text) occupies in a viewer's visual space. In order to determine this angle, the size of the object and the distance that of the viewer from the object are both accounted for. One example consensus value for the critical print size for normally sighted readers to decipher text is 0.2° x-height.

In various implementations, a visual angle of a viewer may be determined using an x-height of the font being displayed, a PPI scaling factor, and a distance of the viewer. As an example, if the font is Arial at 14 points, with an x-height of 51%, Windows assumes a 96 PPI screen, and the text is viewed from 16 inches away (a typical distance on a laptop), the perceived x-height is 0.22°. This is a decent font size and should be readable given because the perceived x-height is greater than the deciphering threshold of 0.2. As another example, a 15.0 font size in points multiplied by a 0.51 x-height ratio, multiplied by a 96/166 PPI factor (e.g., a Windows OS 96 factor on a laptop using a 166 factor), provides an x-height of 4.42 in physical points. In order to calculate the visual angle, a distance of 16 inches multiplied by 72 points per inch provides 1152 points for the distance, which results in a perceived x-height of 0.22 degrees.

Referring again to FIG. 5, at 520 control determines a distance of the viewer from the screen. Additional details of how the viewer distance is determined are described further below with reference to FIG. 6. Once the distance of the user is determined, control continues at 524, where a deciphering threshold is determined. The deciphering threshold may be determined based on the perceived x-height and the distance of the user from the screen. Control in FIG. 5 then ends.

Figure 6:
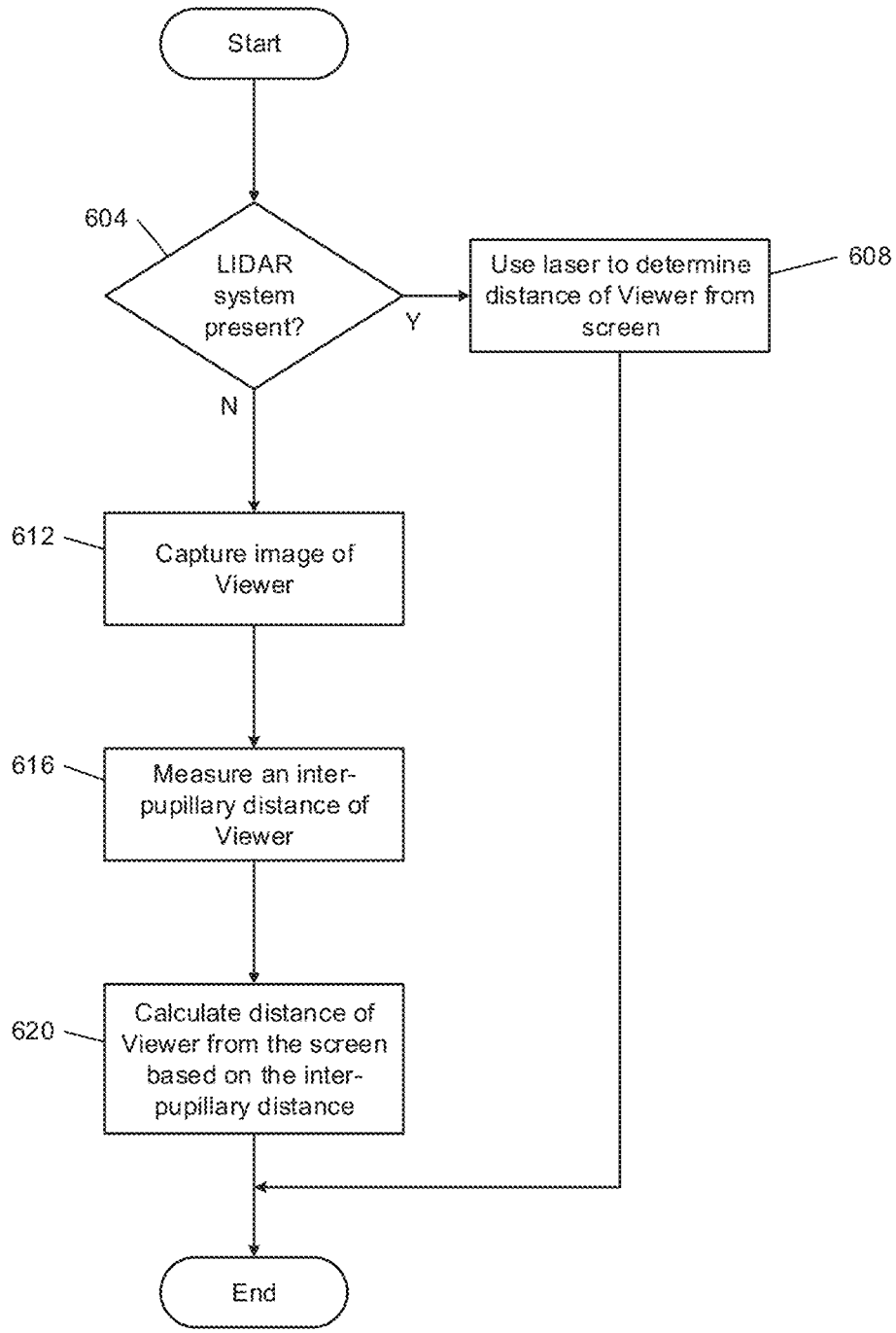
FIG. 6 is a flowchart depicting an example method for determining a distance of a user from a screen.

FIG. 6 illustrates an example method for determining a distance of a user from a screen. Determining the distance of an individual may be performed using software and/or hardware approaches. For increased accuracy, a hardware LIDAR (Light Detection and Ranging) module can be applied in addition to a front facing camera of a device. LIDAR is a laser that records the time it takes for a given signal to return to its source. The LIDAR module emits pulses (similar to sonar), where the time for return of the initial signal is measured in nanoseconds. This technology has been implemented in automatous vehicles, drones, now consumer products such as tablets and smartphones, etc.

A more cost-effective solution may use a software implementation, which can be accomplished with any suitable standard high-resolution camera. A common approach identifies the inter-pupillary distance (e.g., a distance between a viewer's eyes) in order to calculate a distance of the viewer from a screen. The inter-pupillary distance may have such a small variation between people that it is suitable for use in approximating the distance between the viewer and the screen.

One example implementation is fine-grained detection of face-screen distance on smartphones. For example, L may be the inter-pupillary distance of a person, D is the distance between a viewer and a screen, E is an inter-pupillary distance in a photo taken by a front-facing camera, W is a width of the photo as taken by the front facing camera, and the visual angle may be equal to 2*arctan (size of object/2*distance of object). The width of the object is known. Therefore, to get the angle of the inter-pupillary distance L, the maximum width of the camera may be normalized to the width of an object in the photo (e.g., the viewer's inter-pupillary width). This provides the angle width of the object in the camera view, which may be used to obtain the distance D of the viewer from the screen.

Referring again to FIG. 6, control begins at 604 by determining whether a LIDAR system is present. If control determines at 608 that a LIDAR system is present, control proceeds to 608 to use the laser to determine a distance of the user from the screen. If control determines at 604 that a LIDAR system is not present, control proceeds to 612 to capture an image of the viewer. Control then measures an inter-pupillary distance of the viewer at 616, and calculates a distance of the viewer from the screen based on the inter-pupillary distance at 620.

Figure 7:
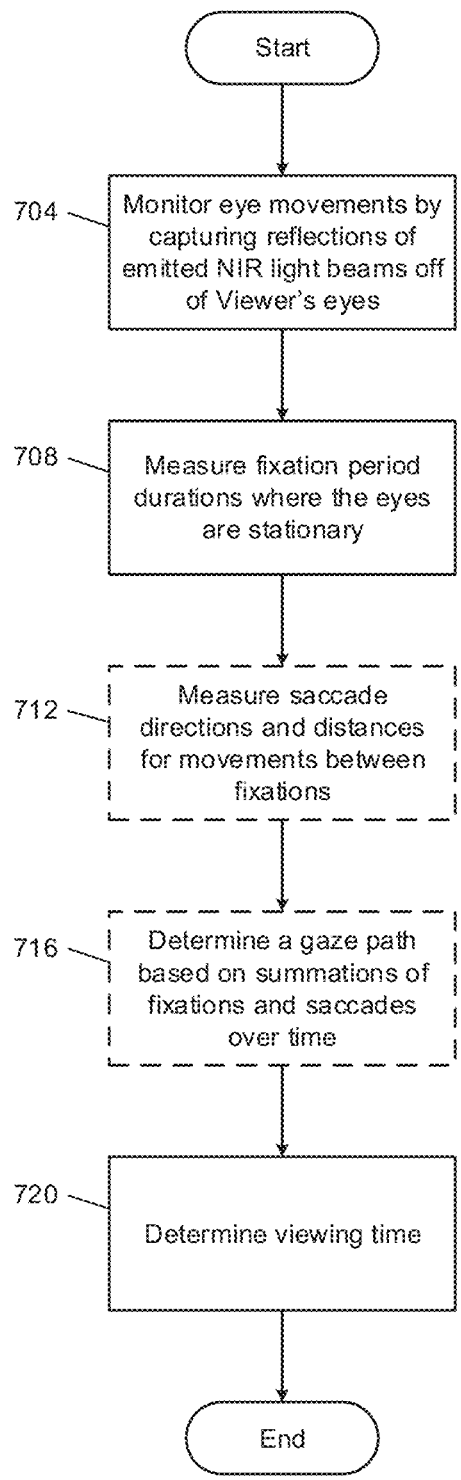
FIG. 7 is a flowchart depicting an example method for determining whether a viewing time of the viewer's gaze is greater than a deciphering threshold.

FIG. 7 illustrates an example process for determining whether a viewing time of the viewer's gaze is greater than a deciphering threshold (e.g., if the viewer is looking at the text long enough to be able to understand the text). The analysis of screen related eye movement may include multiple factors, such as fixation, saccades and gaze paths. Fixations are periods when the viewer's eyes are relatively stationary because the viewer is taking in information. Fixations often range in duration from 60 milliseconds when reading, to several hundred milliseconds when examining photographs or images. Some of the most commonly used fixation-related metrics are number of fixations, number of fixations on each Area of Interest (AOI), total number of fixations, average fixation duration, total fixation duration, time to first fixation, and number of repeat fixations. In various implementations, the fixations may be the most significant factor for determining a viewer's gazing time in order to decide whether to obscure a piece of content on a given screen. The average fixation takes about 225 ms when reading silently, although common ranges may be typically anywhere between 100 and 500 ms.

Saccades are rapid eye movements that occur between fixations. They represent periods of visual search, during which specific information acquisition is not taking place. The direction and distance of saccades are may be indicators of shifts in understanding, attention, or goals. These can be studied to determine if a viewer is actively attempting to gain an understanding of a screen's content. Gaze paths represent a summation of fixations and saccades over time. Straight and rapid gaze paths may indicate efficient and targeted visual navigation of the stimulus, while longer, more circuitous routes often signify confusion or a lack of direction by a viewer. The gaze paths may be monitored to determine whether a viewer's gaze path has passed over a screen, which may indicate that secure content does not need to be obscured. Gaze paths may be analyzed to determine whether a viewer is trying to focus on or understand the contents on a given screen. In various implementations, fixations of greater than 200 ms may indicated that a viewer is trying to read content on the screen.

Referring again to FIG. 7, control begins at 704 by monitoring eye movements, by capturing reflections of emitted NIR beams off of a viewer's eyes. At 708, control measures a fixation period where the eyes are stationary. Control may then proceed to optional steps 712 and 716, which include measuring saccade directions and distances for movements between fixations, and determining a gaze path based on summations of the fixations and saccades over time. At 720, control determines a viewing time of the viewer, which may be based on the measured fixation period durations of stationary eyes, may include saccade direction measurements and gaze path determinations, etc.

Secure and Non-Secure Content Obfuscation System

Figure 8A:
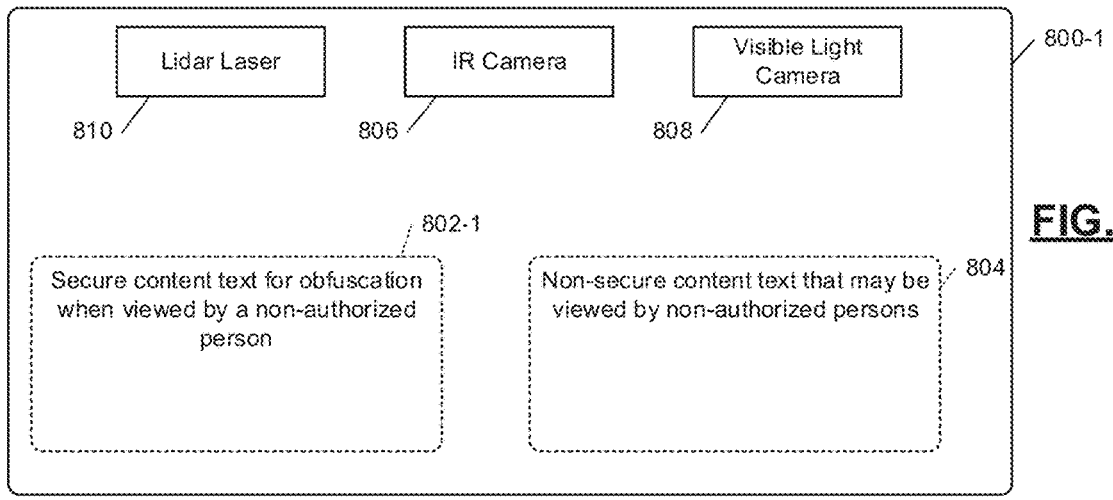
FIGS. 8A, 8B, and 8C are functional block diagrams depicting systems for automated viewpoint detection and screen obfuscation of secure content as well as example illustrations of that obfuscation.
Figure 8B:
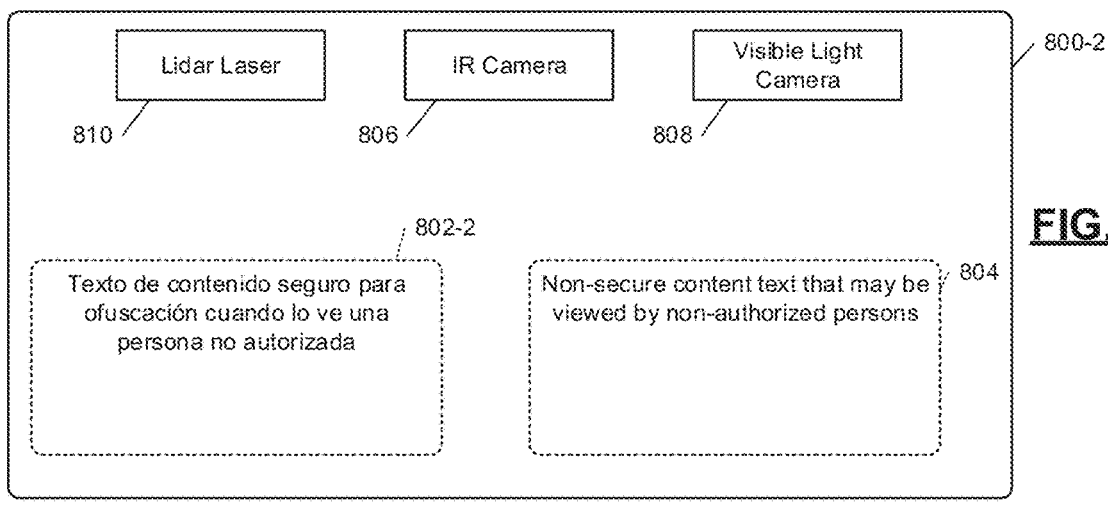
Figure 8C:
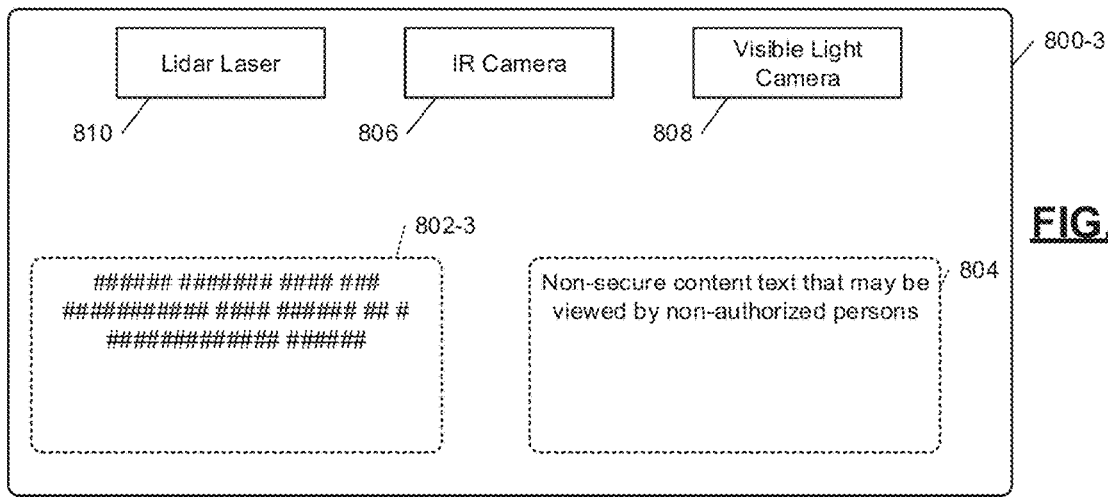

FIGS. 8A-8C illustrate an example system for screen obfuscation. As shown in FIG. 8A, a system 800-1 includes an IR camera 806, a visible light camera 808 and a LIDAR laser 810. Although FIG. 8A illustrates three different cameras and lasers, other implementations may include more or less cameras and/or lasers, other types of cameras and/or lasers, etc. The system 800-1 includes secure content text 802-1, which is obfuscated when viewed by an unauthorized person. The system 800-1 also includes non-secure content text 804, which may not be sensitive and may be allowed to be viewed by unauthorized persons.

FIG. 8B illustrates the system 800-2 where the secure content text 802-2 has been translated to obfuscate the secure content text 802-2 from an unauthorized viewer. For example, in response to detecting an unauthorized viewer, the secure content text 802-2 may be displayed in a translated form. This may allow an authorized viewer that understands the translation language to continue viewing the secure content text 802-2, while inhibiting the unauthorized viewer from recognizing that the secure content text 802-2 has been obfuscated. The non-secure content text 804 may continue to be displayed normally, because it is acceptable for the unauthorized viewer to read the non-secure content text 804.

FIG. 8C illustrates the system 800-3 where the secure content text 802-3 is obfuscated by blurring the words or changing them to symbols. For example, in response to detecting an unauthorized user, the system 800-3 may convert the secure content text 802-3 to symbols to prevent the unauthorized user from reading the words, but the symbols will also inhibit an authorized user from reading the words, and the symbols may make it obvious to the unauthorized user that the words are being obfuscated.

In various implementations, a secure context may include any portion of a screen, document, etc., that a user may want to be protected from an unwanted party (e.g., an unauthorized viewer that is not in the validation set). This secure context may define bounds for the system to obscure portions of the screen. The obfuscation techniques may be applied by executing a translation of a character set to a randomized sequence, a different language which the validated user understands, etc. This may lead to the unauthorized user not being able to understand the contents, while also not immediately noticing that the secure text has been changed. For a more evident approach, secure contents may be blurred, including images and video content.

An application level approach for screen obfuscation may be taken from an Open Document Format (ODT), where a number of zipped files are bundled together and a primary source of the files is content.xml. This context file may include the actual (non-binary) content of the document, where styling may be applied. A dedicated style tag may be generated that is similar to those found in formatting attributes. As an example, a setting may be style-name="Secure-Context". These styles may then be represented similar to any other tag within the document, based on example code below.

```
<text:h style-name="Heading_2">This is a title</text:h>
<text:p style-name="Text_body"/>
<text:p style-name="Secure-Context">
```

This is a paragraph. The formatting information is in the Text body style. The empty text:p tag above is a blank paragraph (an empty line).
</text:p>

As another example application, a web browser-based solution may be implemented. In this approach, web application source code may use an allocated 'data-secure-context' attribute on the document element that the user wishes to obfuscate. HTML is designed with extensibility in mind for data that should be associated with a particular element, but may not have any defined meaning. The feature 'data-* attributes' may allow for storing extra information on standard, semantic HTML elements, without using non-standard attributes, extra properties on DOM, Node.setUserData( ), etc. Using a predisposed attribute may allow for parsing of the source code, such that secure contexts can be identified. Example HTML code is provided below.

```
<!DOCTYPE html>
<html>
<head>
<title>This is the title</title>
</head>
<body>
<h1>Application heading</h1>
<p data-secure-context> This is a secure paragraph.</p>
</body>
</html>
```

An end-to-end system design for a browser-based implementation may be used as a general solution that is extensive to all web content that can be rendered in a browser. For example, a browser extension may be built with a webpage precondition of using an allocated data-secure-context attribute on the element that the user wishes to obfuscate. If a more furtive method of obfuscation is desired, a translation method may be enabled. This approach may translate secure text to another language, or to a randomized character set if desired. In order to enable this capability, upon loading of the webpage's content, all text within secure content portions of the page may be aggregated and supplied to a cloud-based translation service (e.g., Amazon Translate), in order to obtain associated translations. These translations may be stored in a client side cache of secure translations.

The coordinates of a viewer's gaze relative to a viewport may then be obtained. In web browser terms, the viewport is the portion of the web document that is currently viewable on the screen relative to the entirety of the page. Content outside of the viewport is not visible until scrolled into view. In various implementations, the Tobii implementation's analytical SDK may be used to retrieve browser specific x,y coordinates of the browser's viewport. As another alternative, a software-only solution may include using an open sourced browser-based solution such as Webgazer, which can also provide these coordinates.

The coordinates of the element are then mapped to actual document elements of the application. As an example, the elementFromPoint( ) method—often available on both Document and ShadowRoot objects of a web document—may return a topmost Element at the specified coordinates (relative to the viewport). A determination is then made to see if the element is nested within a secure context. The closest( ) Javascript method may traverse the Element and its parents (heading toward the document root), until it finds a node that matches the provided selector string. The call may return itself or the matching ancestor. If no such element exists, the call may return null. The call return may be applied to the 'data-secure-context' attribute.

In various implementations, altering the secure content may include storing an initial value of the secure content in memory, and setting the secure content to the obfuscated version using Javascript's innerHTML( ) function. This secure value may be the translation of secure content text, a redaction view (e.g., black bars, pixilation using style sheets), etc. When the unauthorized viewer looks away from secure content, the secure content may be reset to its initial value.

As described above, the decision of whether to obfuscate text may be based on a variety of factors. For example, a viewer's visual angle may have to be determined as $>=0.2$ degrees prior to obfuscating content. This visual angle may be determined according to a distance that a viewer is located from the contents of a screen. If the viewer has viewed the screen for at least a threshold duration to be able to decipher content (e.g., 150 ms), obfuscation may be implemented. Using a minimum deciphering threshold period may prevent unwanted obfuscation when a minor or unintentional gaze path occurs briefly across a screen.

In various implementations, semantic analysis may applied to identify PHI/PII content in order to dynamically apply secure content regions across any textual document. The obfuscation techniques may be used to remove rows from a spreadsheet that are not relevant to a current viewer, such as rows containing PHI/PII data, usernames/passwords, other ancillary secure contents, etc. Pharmacy operations may require that some systems are accessed only by licensed pharmacists, and obfuscation techniques described herein may allow only valid users to view sensitive screen contents, while unlicensed individuals are inhibited from viewing sensitive content. When mobile devices are left on an office desk, public table, etc., obfuscation techniques described herein may be used to inhibit viewing of spontaneous notification contents that may occur at unexpected times, such as work emails, text messages from co-workers, etc.

In various implementations, secure content regions may be preserved within documents that are sent or received between different users. For example, storing a validation set of authorized users on a remote server may enable multi-device usage of the secure obfuscation system, such that when a document is transmitted to another individual via email, file sharing, etc., the secure obfuscation may be preserved on additional devices. After the recipient has used their IR camera to "validate" their authorization, secure content regions may be unlocked for the authorized individual, while the secure content is still protected from unauthorized viewers in the remote user's environment.

As additional examples, images of unverified users that are attempting to view secure content may be captured to monitor for repeat offenders, 'Big-Board' monitors (such as those within corporate headquarters) may be protected with obfuscation when visitors are passing through these types of spaces, etc. In various implementations, audio data may be obfuscated where the contents of a conversation would only be able to be deciphered by those authorized listeners who are allowed to participate in a given discussion. Validation sets may be established via voice recognition of a statement, and the set of participants may then be validated via voice verification as they join the call. The protected audio content may be triggered via an audio keyword that marks the beginning and end of a secured portion of a given conversation. Users who are not in the validation set may then hear obfuscated discussion, prerendered discussion (in an attempt to conceal the obfuscation), etc. This approach may be used in any suitable audio context, such as sensitive conference discussions including earnings calls, executive decision meetings, etc.

Smart Mirror System

FIG. 9 illustrates an example smart mirror system 900. As shown in FIG. 9, the system 900 includes an infrared (IR) touch panel, a mirror, and a liquid crystal display (LCD) panel. The IR touch panel, mirror and LCD panel may be positioned relative to one another in any suitable arrangement, such as stacked one on top of another in any order, overlaid in parallel, etc. For example, a mirror may be placed over an LCD panel, where the mirror allows a viewer to see images from the LCD panel through the mirror while also seeing a reflection of the viewer in the mirror.

The mirror may be a two-way mirror that allows images to be transmitted through the mirror from one direction while also reflecting images from the opposite direction, which may also be referred to as a one-way mirror, one-way glass, half-silvered mirror or semi-transparent mirror. For example, the mirror may include a partially reflective, partially transmissive coating. The LCD panel may be positioned behind the mirror. In various implementations, any other suitable display device screen may be used, such as a light emitting diode (LED) display, an organic LED (OLED) display, etc. The screen may have any suitable shape or size, and may constitute all or a portion of the area of the mirror. As described above, the mirror may be a reciprocal mirror that appears reflective on one side and transparent on the other. The perception of one-way transmission may be achieved when one side of the mirror is brightly lit and the other side is dark. The glass may be coated with, or have encased within, a thin and almost-transparent layer of metal (e.g., a window film containing aluminum). The mirror may have a surface that reflects some light and is penetrated by the rest of the light.

The IR touch panel may use light emitting diodes and sensors that are embedded in a bezel around the mirror, and emit and detect rows and columns of infrared light across the face of the mirror. This creates an invisible grid of infrared beams, and on the opposite side of the mirror from the emitters, photodetectors or sensors identify touches when the plane of the grid is broken by a finger touch (or other solid object). In other words, infrared touch screens may operate on the basis of light-beam interruption, commonly referred to as beam break, to determine the location of touch events. Although FIG. 9 illustrates an IR touch panel, in various implementations other touch sensing approaches may be used, such as capacitive touch sensors, etc.

As shown in FIG. 9, the system 900 includes a visible light camera 902 and a microphone 904. As described further below, the visible light camera 902 may be used to capture an image of a viewer for facial recognition, and the microphone 904 may be used to authenticate a viewer by voiceprint recognition, to receive voice commands from a user, etc. The system 900 also includes a near-field communication (NFC) reader 906 for reading NFC chips to authenticate a user, to obtain use login information from a user, etc. The system 900 further includes a network interface 908 that connects the system 900 to a health data server 912 via the Internet 910.

Figure 10:
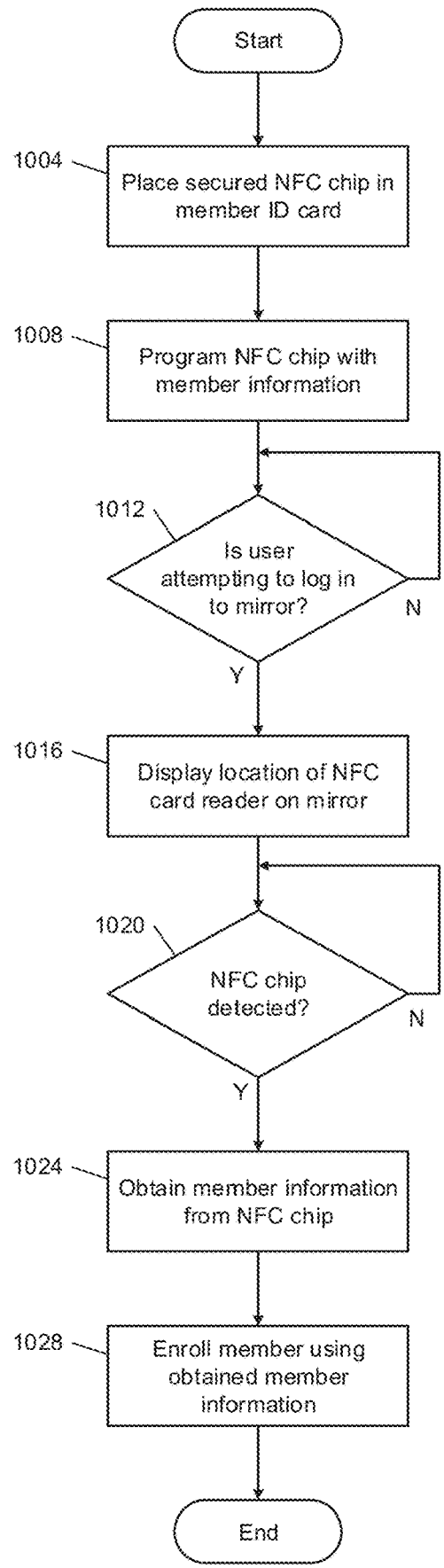
FIG. 10 is a flowchart depicting an example method for enrolling a user via the smart mirror system of FIG. 9.

FIG. 10 illustrates an example process for enrolling a user via the system 900. Control starts at 1004 by placing a secured NFC chip in a member ID card. For example, a health plan administrator, a company, etc., may provide a member ID card to its members or employees that includes an NFC chip. At 1008, control programs the NFC chip with member information.

At 1012, control determines whether a user is attempting to login to the mirror. If not, control continues to wait at 1012. If control determines that a user is attempting to login to the mirror, control proceeds to 1016 to display a location of the NFC card reader on the mirror. For example, the LCD panel may display a location of the NFC reader 906 so that a user knows where to place their member ID card that includes the NFC chip.

At 1020, control waits to detect the NFC chip. Once the NFC chip is detected (e.g., the member ID card including the chip is placed next to the NFC reader 906), control proceeds to 1024 to obtain member information from the NFC chip. At 1028, control enrolls the member using the obtained member information (for example, by communication the member information with the health data server 912 via the network interface 908 and the Internet 910).

As described above, after a user purchases a smart mirror such as the system 900, in order for the user to connect the system 900 to a health network (such as the health data server 912), user previously had to login using a username and password, etc. This was a cumbersome process to type in a username and password at the smart mirror, and also introduced a security issued if another family member was standing nearby during enrollment and watched the user enter the login credentials at the mirror.

In various implementations, a secured and preprogrammed NFC chip is provided in each health plan ID card, where the NFC chip stores member information. The card may be locked down so that only an NFC reader approved by a health plan administrator (which is located in the smart mirror), can read the NFC chip. For example, the NFC reader 906 may be located at the corner of the smart mirror of the system 900, and the location of the NFC reader 906 may be displayed in order to assist the user in placing the member ID card at the appropriate location on the smart mirror. When user is ready to enroll, the user can simply tap the member ID card at the mirror prompt to enroll the user (for example, by associating the member information with the smart mirror and the health data server 912).

As described above, the system 900 may provide a common household utility (e.g., mirror) that is integrated with the health data server 912. The system 900 may provide an easy to use device that integrates and monitors user health and benefits data. The system 900 may integrate several emerging technologies into one useful platform, such as facial recognition, face detection, touch commands, voice commands, integration with health data, etc.

In various implementations, the system 900 may automatically recognize the user and log events over time, similar to a fitness tracing device such as a watch, just by the user standing in front of the smart mirror. The mirror may have access to medical information of the user via the health data server 912, and may be able to inform a user of how their medical information is progressing with respect to various medical conditions of the user. Each user characteristic may be tracked and shared with the user, a clinical advisor, etc., to ensure that the client is adhering to prescribed treatments or physical therapy plans. Example user characteristics and conditions include weight changes, eye color (e.g., to decipher blood pressure or jaundice), therapy progression for scoliosis, body alignment, muscle atrophy/distribution (e.g., left arm smaller/bigger than other), etc. Additionally, or alternatively, Internet-of-Things devices such as fitness tracking watches, etc., may be integrated with the smart mirror to display training data so the user can see progression each day before and after exercise.

The system 900 may allow for therapies to be analyzed in real-time, where an animated version of the user is displayed in the mirror (e.g., a ghosted image effect) to show correct methods for stretching or exercise techniques. The image may display a person's ideal form of an exercise/stretch in relation to their actual progress, and provide encouragement or congratulations depending on the result. This feedback can be analyzed via the mirror's facial imagery for mood analysis to judge adherence likelihood in the future. In various implementations, the system 900 may work with clinicians to obtain prescribed activities, with automatic logging via snapshots or progress and physical activity. Add-ons may be developed to further train and verify data in order to obtain a visual representation of multiple metrics that are increasing/decreasing, such as a scale, a glucose meter, and integrated thermometer, a blood pressure machine, etc.

Figure 11:
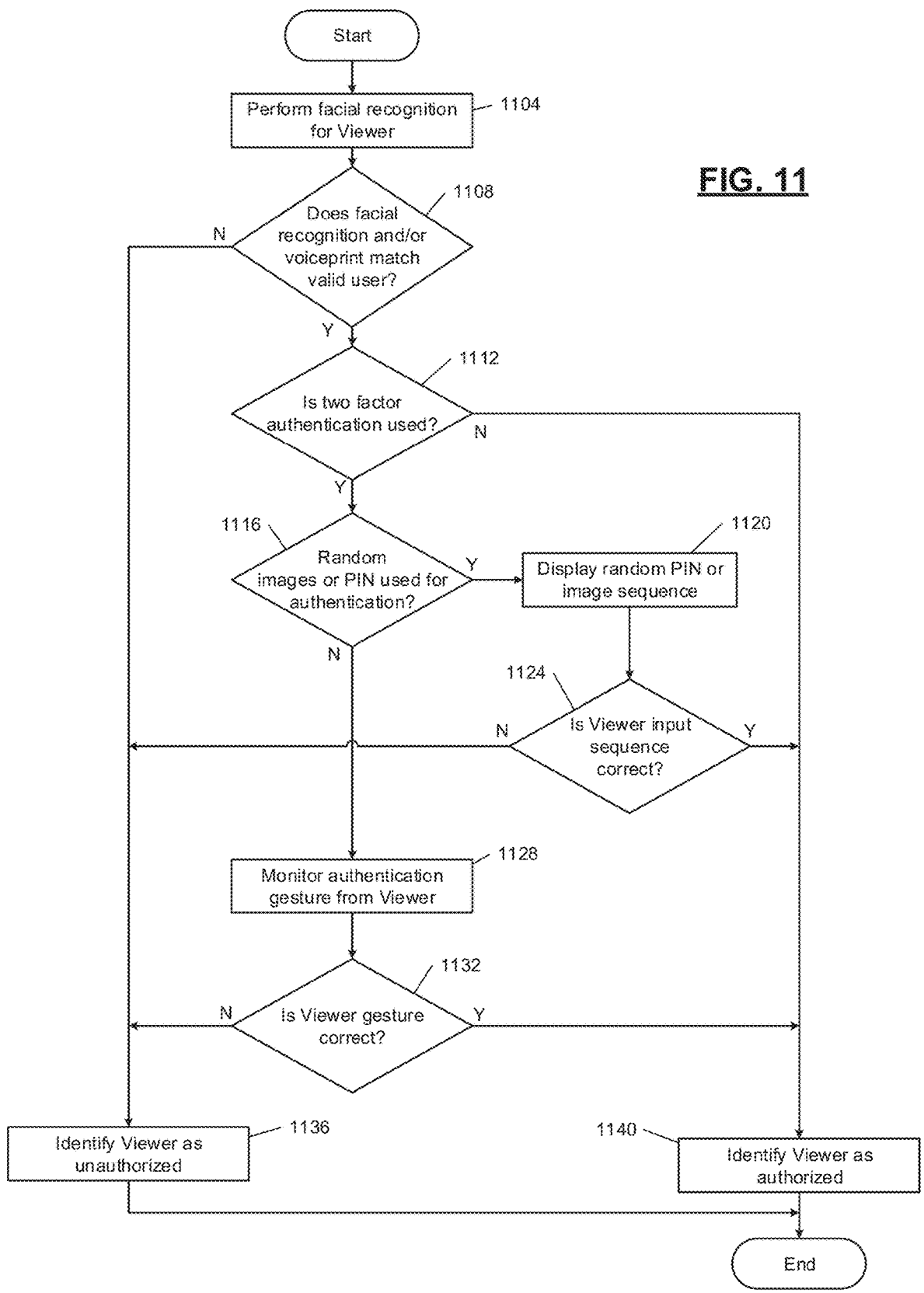
FIG. 11 is a flowchart depicting an example method for authenticating a user to the smart mirror system of FIG. 9.

FIG. 11 illustrates an example method for authenticating a user (e.g., authenticating a user to the smart mirror of the system 900, etc.). At 1104, control begins by performing facial recognition of the user (e.g., using the visible light camera 902, etc.). At 1108, control determines whether the facial recognition and/or voiceprint recognition matches a valid user. For example, control may capture a voiceprint signature of the user in addition to the visible light image for facial recognition, instead of the visible light image for facial recognition, etc. If the facial recognition and/or voiceprint recognition does not match a valid user, control proceeds to 1136 to identify the user as unauthorized. In various implementations, any captured biometric marker (or combination of markers) may be used to authenticate a user, including a fingerprint, an iris scan, a voice, etc.

If control finds a match at 1108, control proceeds to 1112 to determine whether two factor authentication is used. If not, control proceeds to 1140 to identify the user as authorized. If control determines that two factor authentication is used at 1112, control proceeds to 1116 to determine whether a random sequence of images or a PIN number will be used for authentication. If so, control displays the images or PIN digits in a random sequence at 1120. Control then receives input from the user (e.g., by touch inputs detected by the IR touch panel), and determines whether the user input sequence in correct. For example, the user may select a particular sequence of images, or input a particular PIN number, that is matched against stored credentials for the user. Randomizing the display of the images or PIN digits may prevent an unauthorized user from looking at fingerprints on the mirror to obtain the authorized user's password. If control determines at 1124 that the viewer input sequence is correct, control proceeds to 1140 to identify the viewer as authorized. If control determines at 1124 that the viewer input sequence is not correct, control proceeds to 1136 to identify the viewer as unauthorized.

If control determines at 1116 that a PIN or image sequence will not be used, control proceeds to 1128 to monitor an authentication gesture from the viewer. At 1132, control determines whether the motion gesture is correct. If so, control identifies the viewer as authorized at 1140. If not, control identifies the viewer as unauthorized at 1136. Although FIG. 11 provides specific types of authentication methods in certain orders, various implementation may use more or less (or other) authentication methods, may use authentication methods in different orders, etc.

As described above, various implementations may use facial recognition and two factor authentication, to identify a member when the member steps in front of the mirror. For example, when a user enrolls by tapping their member ID card at the NFC reader 906, the visible light camera 902 may capture one or more images to register the member to the smart mirror of the system 900. The member may have the ability to add another factor of authentication such as voice pattern, icon grid, PIN, etc. Once registration is complete, anytime a user steps in front of the mirror, facial recognition may be used to automatically log in the member. When the member steps away from the mirror, the member may be logged off automatically. Personal Health Information (PHI) may be displayed only while the user is logged in, which may make the mirror convenient for a family with multiple members.

As another example, the multi-factor authentication may use an icon grid instead of a PIN. For example, in the smart mirror context a PIN may have issues such as fingerprints on the screen revealing numbers used for the PIN, members tending to forget long PINs, etc. In various implementations, a member may select pictures from an icon-based grid, instead of a PIN. During enrolment, the member may select a few favorite icons in a sequence that creates a story, which the member can easily remember. During normal use, the member selects the same image sequence from the icon grid. The icons are shuffled each time they are rendered, so that fingerprints do not reveal the locations of the images. In addition, or alternatively, gesture-based solutions such as blinks, winks, opening of the mouth, etc., may be used for multi-factor authentication.

When the mirror is displaying data for one member, if another user walks in, the additional user could potentially see the first member's private information. In various implementations, in addition to facial recognition, the system 900 may also track the number of people standing in front of the mirror, such as by counting the number of faces that are seen in view of the mirror. The system 900 may be configured to hide all private information when the number of people standing in front is more than one. Additionally, or alternatively, the system 900 may use example obfuscation techniques to obfuscate secure content when unauthorized viewers are detected. The system 900 may be configured to log out a member no person is in the view of the mirror for a specified time period, such as a few seconds.

Figure 12:
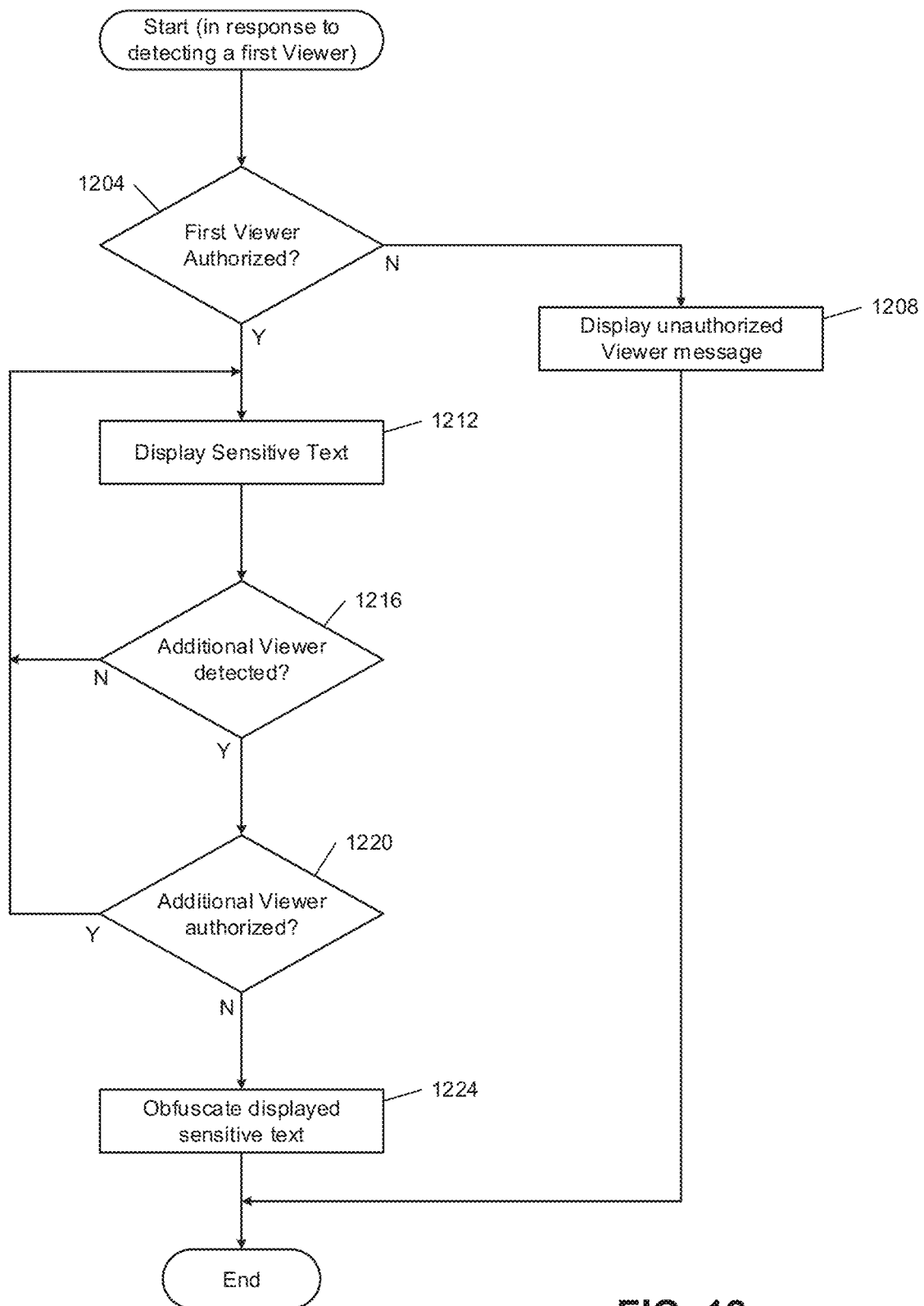
FIG. 12 is a flowchart depicting an example method for providing screen authorization and obfuscation for multiple users at one time.

FIG. 12 illustrates an example method for providing screen authorization and obfuscation for multiple users at one time. Control beings in response to detecting a first viewer, and then determines at 1204 whether the first viewer is authorize. For example, any of the authentication methods described herein (or any other suitable methods) may be sued to determine whether the first viewer is authorized at 1204. If the viewer is not authorized, control proceeds to 1208 to display an unauthorized viewer message.

If control determines at 1204 that the first viewer is authorized, control proceeds to 1212 to display sensitive text (e.g., secure content text, etc.). At 1216, control determines whether an additional viewer is detected. If not, control continues displaying the sensitive text at 1212 while waiting to detect an additional viewer. If an additional viewer is detected at 1216, control proceeds to determine whether the additional viewer is authorized at 1220. If the additional viewer is authorized at 1220, control returns to 1212 to continue displaying the sent vie text and waiting to detect additional viewers. If control determines at 1220 that the additional viewer is not authorized, control proceeds to 1224 to obfuscate the sensitive text.

As described above, the obfuscation system may be a multi-user system with the capability to classify multiple valid users. Each authorized user may be provided with a unique authentication access token, which may include authenticating multiple security tokens to a single endpoint (in contrast to existing security mechanisms that account for only a single user using either a username/password combination and/or a biometric as input). For example, existing authentication approaches prevent two users from simultaneously logging into a single financial account system from a single user interface. An advantage of the example multi-user approaches described herein is that if a user is utilizing multiple devices simultaneously, the user may be logged out of any other devices for added security, by having those accesses rejected. In addition, content on the screen can be uniquely tailored to the set of viewers which are using the system, so that any assets requiring dual access to manipulate (e.g., joint banking accounts, etc.), may be accessed at once by multiple authorized users.

In various implementations, a system may compare a combination of detected features of at least two detected viewers to a plurality of multi-user set entries in the authorized user database. One or more secure content portions may be displayed with obfuscation by default until all members of one of the multi-user set entries are detected at the viewing proximity location with respect to the screen. The secure content portions may be obfuscated in response to detection of an unauthorized viewer in addition to all detected members of the multi-user set entry.

Example applications include a team of employees being able to read PHI, while an intern or an unauthorized employee is be restricted from viewing lines of a spreadsheet that have PHI in them. Two people who are co-owners of a shared account could view a banking application at the same time, while other unauthorized viewers would be shown obfuscated text. Authorized application developers may be able to see confidential code in groups, while unauthorized viewers have the confidential code obfuscated.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. The phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module. For example, the client module may include a native or web application executing on a client device and in network communication with the server module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A system comprising:
a screen configured to display documents for viewing by at least one authorized user;
memory configured to store computer-executable instructions, an authorized user database, and a document properties database; and
at least one processor configured to execute the instructions, wherein the instructions include:
identifying one or more secure content portions of a document to be displayed on the screen, according to the document properties database;
displaying the identified one or more secure content portions without obfuscation when no authorized viewers and no unauthorized viewers are detected;
detecting a viewer at a viewing proximity location with respect to the screen;
determining whether the detected viewer is authorized to view the secure content portions according to the authorized user database; and
in response to a determination that the detected viewer is not authorized to view the secure content portions:
determining a gaze location of the unauthorized viewer on the screen; and
in response to the gaze location encompassing the identified one or more secure content portions of the document, obfuscating the identified one or more secure content portions of the document, wherein the identified one or more secure content portions are displayed without obfuscation when the authorized viewer is detected, and with obfuscation when the unauthorized viewer is detected at the viewing proximity location with respect to the screen with the determined gaze location encompassing the identified one or more secure content portions of the document.

2. The system of claim 1 wherein:
the instructions further include:
obtaining a translation of the identified one or more secure content portions of the document, and storing the translation in the document properties database; and the obfuscating includes displaying the translation of the identified one or more secure content portions of the document.

3. The system of claim 1 wherein:

the obfuscating includes rendering the identified one or more secure content portions of the document illegible;

the document includes one or more non-secure content portions; and the obfuscating includes leaving the one or more non-secure content portions legible.

4. The system of claim 1 wherein:

the obfuscating includes removing at least one of the identified one or more secure content portions from the screen; and the instructions further include displaying the removed at least one secure content portion from the screen in response to a detection that the unauthorized viewer has left the viewing proximity location with respect to the screen.

5. The system of claim 1 wherein determining whether the detected viewer is authorized includes at least one of:

capturing an infrared thermogram of the detected viewer and comparing the captured infrared thermogram to entries in the authorized user database;

capturing a visible light image of the detected viewer and comparing the captured visible light image to entries in the authorized user database;

capturing a biometric marker of the detected viewer and comparing the captured biometric marker to entries in the authorized user database;

displaying multiple images or multiple numbers in a random pattern on the screen, receiving an input selection sequence of the multiple images of the multiple numbers from the detected viewer, and comparing the input selection sequence to entries in the authorized user database; and capturing a motion gesture of the detected viewer and comparing the captured motion gesture to entries in the authorized user database.

6. The system of claim 1 wherein the determining the gaze location of the detected viewer includes:

emitting an infrared light beam;

capturing a reflection of the infrared light beam using one or more cameras; and filtering and triangulating the captured reflection to identify the gaze location of the detected viewer.

7. The system of claim 1 wherein:

the detecting includes detecting at least two viewers at the viewing proximity location with respect to the screen;

the determining whether the detected viewer is authorized includes determining whether a set of the at least two detected viewers is authorized, by comparing a combination of detected features of the at least two detected viewers to a plurality of multi-user set entries in the authorized user database; and the instructions further include:

displaying the identified one or more secure content portions with obfuscation by default until all members of one of the multi-user set entries are detected at the viewing proximity location with respect to the screen; and obfuscating the identified one or more secure content portions in response to detection of an unauthorized viewer in addition to all members of the one of multi-user set entries.

8. A system comprising:

a screen configured to display documents for viewing by at least one authorized user;

memory configured to store computer-executable instructions, an authorized user database, and a document properties database; and at least one processor configured to execute the instructions, wherein the instructions include:

identifying one or more secure content portions of a document to be displayed on the screen, according to the document properties database;

detecting a viewer at a viewing proximity location with respect to the screen;

determining whether the detected viewer is authorized to view the secure content portions according to the authorized user database;

in response to a determination that the detected viewer is not authorized to view the secure content portions:

determining a gaze location of the unauthorized viewer on the screen; and in response to the gaze location encompassing the identified one or more secure content portions of the document, determining whether a viewing angle of the detected viewer is greater than a deciphering angle threshold, and only obfuscating the identified one or more secure content portions of the document in response to a determination that the viewing angle of the detected viewer is greater than the deciphering angle threshold;

wherein determining whether the viewing angle of the detected viewer is greater than the deciphering angle threshold includes:

calculating an x-height percentage of a font of text in the document;

determining a distance of the detected viewer from the screen; and determining the viewing angle according to the calculated x-height percentage of the font and the determined distance of the detected viewer from the screen.

9. The system of claim 8 wherein determining the distance of the detected viewer from the screen includes at least one of:

using a laser of a LIDAR system, at least in part, to determine the distance of the detected viewer from the screen; and capturing an image of the detected viewer, measuring an inter-pupillary distance of the detected viewer, and calculating the distance of the detected viewer from the screen according, at least in part, to the measured inter-pupillary distance.

10. A system comprising:

a screen configured to display documents for viewing by at least one authorized user;

memory configured to store computer-executable instructions, an authorized user database, and a document properties database; and at least one processor configured to execute the instructions, wherein the instructions include:

identifying one or more secure content portions of a document to be displayed on the screen, according to the document properties database;

detecting a viewer at a viewing proximity location with respect to the screen;

determining whether the detected viewer is authorized to view the secure content portions according to the authorized user database; and in response to a determination that the detected viewer is not authorized to view the secure content portions:
  determining a gaze location of the unauthorized viewer on the screen; and
  in response to the gaze location encompassing the identified one or more secure content portions of the document, determining whether a viewing time of the detected viewer is greater than a deciphering time threshold, and only obfuscating the identified one or more secure content portions of the document in response to a determination that the viewing time of the detected viewer is greater than the deciphering time threshold;
wherein determining whether the viewing time of the detected viewer is greater than the deciphering time threshold includes:
monitoring eye movements of the detected viewer by capturing reflections of emitted infrared light beams off of eyes of the detected viewer;
measuring a fixation period duration during which the eyes of the detected viewer are stationary; and
comparing the measured fixation period duration to the deciphering time threshold, wherein the deciphering time threshold corresponds to a threshold duration of time for a viewer to be able to decipher content.

11. The system of claim 10, wherein the deciphering time threshold is at least 150 ms.

\* \* \* \* \*